United States Patent
Crespo et al.

(10) Patent No.: US 7,823,681 B2
(45) Date of Patent: Nov. 2, 2010

(54) BREATH ALCOHOL IGNITION INTERLOCK DEVICE WITH BIOMETRIC FACIAL RECOGNITION WITH REAL-TIME VERIFICATION OF THE USER

(75) Inventors: Pierre M. Crespo, Burkesville, KY (US); Alex Chan, Kwun Tong (HK)

(73) Assignee: B.E.S.T. Labs, Inc., Boardman, OH (US)

( * ) Notice: Subject to any disclaimer, the term of this patent is extended or adjusted under 35 U.S.C. 154(b) by 0 days.

(21) Appl. No.: 12/595,007

(22) PCT Filed: Oct. 3, 2008

(86) PCT No.: PCT/US2008/078746

§ 371 (c)(1),
(2), (4) Date: Oct. 7, 2009

(87) PCT Pub. No.: WO2009/048809

PCT Pub. Date: Apr. 16, 2009

(65) Prior Publication Data
US 2010/0108425 A1  May 6, 2010

Related U.S. Application Data

(60) Provisional application No. 60/978,961, filed on Oct. 10, 2007.

(51) Int. Cl.
*B60K 28/06* (2006.01)

(52) U.S. Cl. ..................... 180/272; 340/576

(58) Field of Classification Search ............... 180/272; 340/576; 382/104
See application file for complete search history.

(56) References Cited

U.S. PATENT DOCUMENTS 5,729,619 A    3/1998  Puma

(Continued)

*Primary Examiner*—Paul N Dickson
*Assistant Examiner*—Joseph Rocca
(74) *Attorney, Agent, or Firm*—McNees Wallace & Nurick, LLC (57) ABSTRACT

An interlock system using biometrics scans to identify in real-time an individual who seeks to operate a mechanical device, such as an automobile. Biometrics features that uniquely identify an individual are selected. If a real-time biometrics scan of the individual does not match a stored image of an authorized operator, the interlock system will lock the mechanical device to prevent operation. The interlock system may be used in conjunction with a breath alcohol analyzer to determine impairment. If the biometrics testing indicates that the individual is required to be tested for impairment, the mechanical device will not operate until the testing is completed. If the biometrics testing automatically indicates that the operator of the mechanical apparatus and the individual exhaling into the breath alcohol analyzer component of the ignition interlock is not the same person, the ignition system of the mechanical apparatus, which operates in conjunction with the ignition interlock of the present invention, provides a programmable software option to prevent the apparatus from starting. If the test indicates that the individual is impaired the interlock system will lock the mechanical device to prevent operation.

22 Claims, 4 Drawing Sheets

U.S. PATENT DOCUMENTS

| | | | |
|---|---|---|---|
| 6,526,802 B1 | 3/2003 | Fisher et al. | |
| 6,748,792 B1 * | 6/2004 | Freund et al. | 73/23.3 |
| 6,810,309 B2 | 10/2004 | Sadler et al. | |
| 6,898,299 B1 | 5/2005 | Brooks | |
| 6,956,484 B2 | 10/2005 | Crespo | |
| 6,967,581 B2 * | 11/2005 | Karsten | 340/576 |
| 7,256,700 B1 | 8/2007 | Ruocco et al. | |
| 7,400,258 B2 | 7/2008 | Crespo | |
| 7,403,873 B2 | 7/2008 | Okuno et al. | |
| 7,404,311 B2 | 7/2008 | Guth et al. | |
| 7,543,472 B2 | 6/2009 | Crespo et al. | |
| 2003/0117287 A1 * | 6/2003 | Crespo | 340/576 |
| 2006/0237254 A1 | 10/2006 | Mobley et al. | |
| 2008/0046503 A1 | 2/2008 | Okuno et al. | |

* cited by examiner

BREATH ALCOHOL IGNITION INTERLOCK DEVICE WITH BIOMETRIC FACIAL RECOGNITION WITH REAL-TIME VERIFICATION OF THE USER

FIELD OF THE INVENTION

The present invention is generally directed to ignition interlock devices, and specifically to ignition interlock devices used in vehicles to monitor drivers having DUI convictions using biometrics for driver identification, the drivers retaining special operator's driving privileges under court-ordered or other jurisdictional mandates and supervision.

BACKGROUND OF THE INVENTION

Various interlock devices exist to prevent operation of a mechanical apparatus when an operator is mentally and/or physically impaired as a result of consumption of alcoholic beverages. These devices utilize a breath alcohol analyzer device, which determines an alcohol level in an individual's breath that is correlated to the alcohol level in the bloodstream. This determination controls the decision as to whether or not the ignition interlock permits the device or apparatus to engage and start. Most frequently, these interlock devices are utilized on automobiles.

While many of the interlock systems available today can ascertain whether a certain preset breath alcohol reading limit of the person exhaling into the breath alcohol analyzer device has been exceeded or not, these systems suffer from an infirmity in ascertaining whether the individual under court-ordered supervision is in fact the driver, and whether the driver is in fact the person exhaling into the breath alcohol analyzer device.

As a result, technological advances have resulted in innovations in ignition interlock technology. These technological advances endeavor to accurately identify and correlate the individual who is jurisdictionally assigned via an interlock restricted license or as a condition of judicial oversight, such as probation or bond, to operate a vehicle with an ignition interlock under such judicial supervision with the driver and/or with the individual under supervision exhaling into the breath alcohol analyzer device. While prior art devices have sought to achieve these results, they suffer from deficiencies which can allow the unscrupulous to by-pass the intended safeguards.

Prior art devices currently in use utilize photo identification in an attempt to correlate and identify the operator of a vehicle with an ignition interlock. Such devices obtain a single-place, 2-D photographic image of the prospective operator simultaneously with the prospective operator blowing a breath sample into a breath alcohol analyzer device. This image and the results of the breath alcohol analyzer device test are time-stamped and stored for review at a later time. Of course, if the results of the breath alcohol analyzer device test are outside an allowable range, the ignition interlock will engage to prevent vehicle operation. Of course, limitations to these test methods are limited by the ability of the operator to adequately mask or conceal identity.

SUMMARY OF THE INVENTION

The present invention overcomes the infirmities of the prior art by using facial biometrics to positively identify the operator of a mechanical apparatus, such as an automobile, and optionally to identify the individual exhaling into the breath alcohol analyzer device component of the ignition interlock.

The biometrics utilized in this invention measures a characteristic unique to an individual that positively identifies the individual. In its simplest form, the invention utilizes facial biometrics. If the facial biometrics testing automatically indicates that the operator of the mechanical apparatus and the individual exhaling into the breath alcohol analyzer component of the ignition interlock is not the same person, the ignition system of the mechanical apparatus, which operates in conjunction with the ignition interlock of the present invention, provides a programmable software option to prevent the apparatus from starting.

The biometrics testing utilized can be either a three-dimensional (3-D) or four-dimensional (4-D) biometrics infrared facial scan that analyzes the topography of both hard and soft tissue to determine identity. The facial scan of the present invention uses 3-D infrared imaging or 4-D facial biometrics or 'A.F.R.S', Automated Face Recognition Systems. The field of view (FOV) of the scanning device includes at least the full face and head of the individual located in the operator's position of the mechanical apparatus. The FOV of the scanning device ideally also includes the breath alcohol analyzer component of the ignition interlock system, so that the device of the present invention provides real-time identification and verification against an unauthorized user database of operators of the apparatus and not merely a time-dated single-plane photographic record of an operator's image and the operator's blood alcohol level equivalence. The interlock system thus includes an infrared scanning device and breath alcohol analyzer component, both in communication with a CPU (Central Processing Unit), a memory component, which may be a part of the CPU, the interlock system in communication with the ignition system of the mechanical device so that the operation of the ignition system is controlled by the interlock system of the present invention.

The invention provides additional sophistication. For a mechanical apparatus such as a motor vehicle, more than one person may require the use of the apparatus, and this device will allow more than one person to operate the apparatus. Each authorized operator undergoes a 3-D or a 4-D biometrics infrared scan, which creates a 3-D or a 4-D image that is stored in a memory. The 3-D biometrics infrared facial scan of each individual is unique. On operation of a motor vehicle, the individual operating the vehicle will activate the system. This can be done be activating the system, which can be accomplished automatically, by inserting a key in the ignition or by pressing a button, either on the vehicle or as a component of the ignition interlock system. An infrared scanning device focused on the operator's position will scan the face of the person sitting in the operator's position. This scan will be compared to the images stored in memory. If the scan does not match with one of the images of the authorized operators stored in memory, the device can include a programmed owner-selectable option so that the ignition system of the vehicle will be locked out and the vehicle will not start, regardless of whether a breath alcohol analyzer component is included.

If the operator is recognized as an authorized operator, one of two options is available. In the first option, a breath alcohol analyzer component is included as part of the interlock system and the operator is required to exhale into the breath alcohol analyzer device, while being scanned by the scanning device. If either the infrared facial scan of the person exhaling into the breath alcohol analyzer device does not match the operator, a 3-D or 4-D biometrics image stored in memory, or if the breath alcohol analyzer device produces results that indicate the legal levels of intoxication is exceeded, the ignition will remain locked out and the vehicle will not start. Each lock-out can be permanent or may extend for only a predetermined period of time, after which the identification and start-up procedure can be repeated. The system can be programmed so that after a predetermined number of lock-outs, the system is "permanently" locked out. Permanent lock-out means that the ignition system will not operate unless it is reset. A reset procedure may be determined such as by state law or ignition interlock program specification. It may require a return for service recall to an interlock service shop. Alternatively, the system may include radio frequency transmit/receive (RF) capabilities, allowing the system to be reset remotely by a monitoring station using cellular or satellite communication.

The second option can include additional sophistication. Each authorized operator of the apparatus undergoes a biometrics infrared facial scan to create a 3-D or 4-D image that is stored in a memory. An operator of the apparatus, the individual operating it, will activate the system as set forth above. A scanning device focused on the operator's position will scan the face of the person sitting in the operator's position. If the scan does not match an image stored in the memory, then the apparatus will not engage and the apparatus will be temporarily locked out. The system will remain locked out until it matches an individual in the operation position with a stored image. If the system is equipped with a breath alcohol analyzer device and the device is activated, and the operator is recognized as an authorized operator, the system then determines whether the operator is an individual under court-ordered supervision. If the operator is not an individual under court-ordered supervision or holding an interlock restricted license, the ignition lock will be released so that the apparatus can be started, when this option is selected by the owner.

Of course, it will be recognized that the ignition lock system can be inactivated for a predetermined period of time before being reset to the lock setting, to prevent a switch of persons in the operator's seat. Alternatively, the scanning device can repeat the facial scan after the apparatus has been started, but before the apparatus is set in motion (e.g. transmission shifted into gear) to verify that there has been no switch of individuals in the operator's seat. If the system detects such a switch, the apparatus will record a circumvention and cause interlock program violations calling the interlocked apparatus in for early service and reporting. This may require the start-up procedure to be repeated. Depending on the programming, the unit also can be set to immediately shut down the apparatus before it is set in motion.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

The present invention represents an advancement in the ignition interlock device technology. This interlock system is based on an expandable plug-and-play platform for the integration of various technological features as market conditions and jurisdictional specifications require or may require in the future. The present invention may be incorporated into vehicle systems as a theft prevention device with an option of activating the alcohol testing feature.

Biometric Facial Recognition

The ignition interlock device of the present invention uses the latest innovations in biometric facial recognition technology. As noted above, prior art devices are passive in nature, which is to say that they utilize flat, single-plane, 2-D, digital photography image capture of an ignition interlock user and records the captured image and detector readings, usually of breath, along with a time and date stamp, the captured image being reviewed at a later time. Since an ignition interlock breath alcohol test is an unsupervised test, simple image capture is "passive" in that it does not provide a technological ability to 'verifiably auto recognize' an authorized user at the time of the initial breath alcohol test. Therefore, due to an inability to positively identify a user in real-time, this passive image capture cannot prevent an unauthorized user from engaging the interlocked vehicle. Consequently, this passive photo capture system is not an active anti-circumvention device intended to prevent unauthorized users from starting an ignition interlocked vehicle. As used herein, "passive" refers to systems displaying these characteristics. In addition, the available systems cannot positively identify in real-time a named individual sanctioned to use a mandated jurisdiction interlock program.

The facial biometric recognition technology feature incorporated into the ignition interlock of the present invention allows for real-time identity verification from a database comprised of authorized users for a particular serial numbered ignition interlock unit. An unauthorized and unidentified user may be precluded from engaging an interlock device and a sanctioned offender can be compelled to submit to a test for sobriety. As used herein, a facial biometric recognition technology feature that can be incorporated into an ignition interlock includes a scan of a facial biometric of an individual and compares the scan to an image stored in memory, the scan and the stored image uniquely identifying the individual. While any facial biometric may be used, current facial biometrics that can uniquely identify individuals include 3-D and 4-D biometric infrared facial scans and images stored from such scans as well as scans of selected ocular features of individuals and images stored from such scans. Once a user is identified from an initial biometric facial scan result, the interlock will prompt the apparatus to start or may require a breath test, in which case the interlock will prompt the individual for an initial breath test. A second biometric facial scan may be programmed to occur while the identified authorized user is in the process of administering a breath test in the ignition interlock for further confirmation. Further, a biometric facial scan of the authorized user may additionally be performed after the vehicle has been started, for example, while the vehicle is being driven, which may prompt for additional breath tests during intervals of a programmed rolling retest feature.

Furthermore, the data log activity report, which is generated by other passive ignition interlock devices which require a camera capability, can currently record an image next to the time and date stamped activity but without the ability to insert identifiably the user name. Therefore, with single-plane, 2-D, digital image recording technology, positive identification of the imaged user in the data log report can only indiscriminately and accurately identify the imaged user after the fact of vehicle or apparatus operation, when a qualified third party human reviews and confirms the image. Additionally, unless an ignition interlock is summonsed for early reporting, events data log downloads can occur up to 30 to 60 days after the recorded fact. Positive "verification" identification of a user using single-plane, 2-D, digital image capture assumes that the data log events have been downloaded and processed for third party review, which can occur well after the recording of the data and the operation of the vehicle. Passive ignition interlock provides no real-time (positive) identity verification with simple camera-capable interlocks, that enable the placement of a recorded name next to a verified user's data logged activity. The data logged reported activity still remains nameless with the passive ignition interlocks using digital photography interlocks. Specifically single-plane, 2-D imaging is not capable of positive real-time identification and response.

The facial biometric recognition technology feature incorporated into the ignition interlock of the present invention allows for real-time identity verification from a database stored in memory comprised of authorized users, which then enables the authorized users' name to be included as a key factual element of the interlock data log activity report. The present invention also permits an image of the authorized user to appear next to the name and logged data event, depending upon jurisdictional reporting requirements.

Contrary to passive, 2-D photography, digital image capture such as used by Smart Start Inc. of Irving, Tex. in their Model 20/20, and by Interceptor Ignition Interlocks, Inc. of Pawling, N.Y., the present invention utilizes 3-D or 4-D facial geometry and topography techniques and determines a plurality of 3-D or 4-D coordinates. For a biometric infrared facial scan, the infrared range scanner transforms the head into a known view. A 3-D or 4-D mesh and corresponding texture based on these coordinates is acquired and stored.

Three-dimensional imaging utilizes a 3-D infrared device which captures a 3-D profile of an individual using an infrared imaging device utilizing individual wavelengths shorter than visible light wavelengths. Since this radiation detects body features not detectable using visible light, the head of each individual provides a unique profile. Three-dimensional imaging technology is available from sources such as Bioscript of L-I Identity Solutions of Stamford, Conn. or A4 Vision Inc. of Sunnyvale, Calif. Four-dimensional imaging utilizes infrared techniques and visible light images to create a 4-D facial biometrics, or "A.F.R.S.", such as that developed by Titanium Technology of San Jose, Calif. Four-dimensional imaging also utilizes the infrared imaging technology and provides a unique profile of an individual. Four-dimensional imaging is preferred for use in the interlock system of the present invention.

With the use of a miniaturized infrared scanning device in the interlock system of the present invention, a version method similar to confocal laser scanning microscopy combined with Local Feature Analysis (LFA) may be used. This process obtains high-resolution optical facial nodal point measurements, which are then processed through computerized recognition algorithm software, which also can be stored in a memory device and retrieved and run by a CPU, typically the CPU of a computer. The optical facial nodal points of the image stored in the CPU are compared to those of the individual scanned for a match. The computer program compares selected facial features from a real-time live image with a stored image from the facial database. It should be apparent that both the live image and the stored facial database can be represented as a plurality of coordinates in space. Local Feature Analysis is the fundamental of most existing facial recognition. It defines a set of topographic, local kernels that are optimally matched to the second order statistics of the input ensemble. The kernels are derived from the principal component axis, and consist of "sphering" the principal component analysis (PCA) coefficients to equalize their variance, followed by rotation to pixel space. The kernels are found to have spatially local properties and are "topographic" in the sense that they were indexed by spatial location. A new 4-D facial recognition method developed by Titanium Tech uses two-view geometry Dynamic Local Feature Analysis (2VDLFA). This technique employs the LFA on integrated shape, texture and two-view geometry images. The relationship between two views can be explained by 'epipolar geometry', which in turn can be explained by a stereo vision and a third point in-depth that provides a 3-D measurement. Reference points are acquired point-by-point in this fashion to produce an image and reconstructed with a computer or CPU, allowing 3-D reconstructions of topographically complex objects. Infrared laser 3-D scanning uses real-time data capture of distinctive facial features where rigid tissue and bone are most apparent, such as the curves of the eye socket, nose, cheeks, mouth, and chin to identify the subject. These areas are all unique and do not change over time. Using depth and an axis of measurement planes that are not affected by lighting, 3-D facial recognition can be used in darkness and has the ability to recognize a subject at different view angles. The process involves detection, alignment, measurement, representation, matching, and identification verification. Once the 3-D facial recognition system detects a face, the system determines the head's position, size and pose. With an infrared laser, the subject has the potential to be recognized up to 90 degrees in the database has equivalent stored matches. In summary, 4-D facial recognition using 2VDLFA mentioned above, employs two-view geometry images to provide the depth information of the face, which simulate the 3-D nature of the human face. Shape encodes the feature geometry of a face and is extracted by dynamic edge detection. Texture provides a normalized facial feature on the image, which provide one or more dimensions of information to form a 4-D facial recognition. According to experimental tests performed by Japan University, it is believed that the added information present in 4-D data creates the superior performance and recognition authority, which shows that 4-D facial biometrics encompassing 2VDLFA that can separately identify otherwise identical twins.

Current methods of testing for impairment of an operator at the time of operating an apparatus have been limited to using a breath alcohol analyzer device. Human impairment and the side effects such as loss of coordination, loss of alertness, slow and inaccurate neurological response time, and overall poor judgment or even a state of unconsciousness can result from prescribed drugs or illegal narcotics and even extreme fatigue. Human impairment is broad in scope and is not limited solely to impairment cause by the consumption of alcohol. Therefore, other measures to detect other induced sources of impairment or a normal human state of impairment in conjunction with an ignition interlock device at the time of desired operation of an apparatus other than from an alcohol source, are contemplated. Blood and urine analysis are, in practice, too complex or intrusive to be easily and quickly used as a method of impairment detection, especially in an unsupervised vehicle environment.

Two options to address other non-alcohol sources of impairment detection in a vehicle environment or at the start-up of an apparatus can be integrated as an add-on component. A first option used with the present invention ignition interlock is based on a plug-and-play platform of components that can integrate a pupilometer based on EyeCheck™ technology such as is manufactured by EyeCheck™ of MCJ, Inc. of Rockford, Ill. EyeCheck™ aims an infrared light into the pupil causing a stimulus which then detects and measures pupil eye movement and pupil dilation. The proprietary software calculates and measures pupil diameter combined with pupil movement speed, which when compared against a baseline measurement then calculates a status of either failed human impairment or passed non-impairment present. The premise for the technology is largely based on the same technology used by trained Drug Recognition Experts, DRE's, who also examine the subject and determine impairment, in part, on the condition and movement of the pupil. The second option uses saliva testing that can be accomplished by using a Branan Medical saliva drug and alcohol test strip. The saliva test strip such as the Oratect Plus™ strip, made by Branan Medical of Irvine, Calif. also tests for adulterants that would be added to skew the accuracy of any drug or alcohol detection. After the operator swabs his/her mouth for a saliva sample, the strip is then placed in the strip reader unit for results produced in less than 1 minute. The reader independently reads the strip for presence of alcohol or drugs. If the test results are clear then the saliva strip reader sends a message to the ignition interlock allowing the apparatus to engage. If the reader detects a failed test due to a presence of a drug substance in the operator's saliva, the reader will send the data to be recorded in the memory of the ignition interlock and the vehicle or apparatus will be prevented from starting. The use of 4-D facial biometrics and an optional added camera system can record the saliva strip testing procedure to minimize the opportunity for an operator to pursue any means of attempted system circumvention. In conclusion, the current invention addresses the ability to test for 'other than alcohol' sources of human impairment by integrating into the ignition interlock 'plug-and-play' platform either an EyeCheck™ pupil dilation unit or a Branan Medical saliva strip drug reader.

Figure 1:
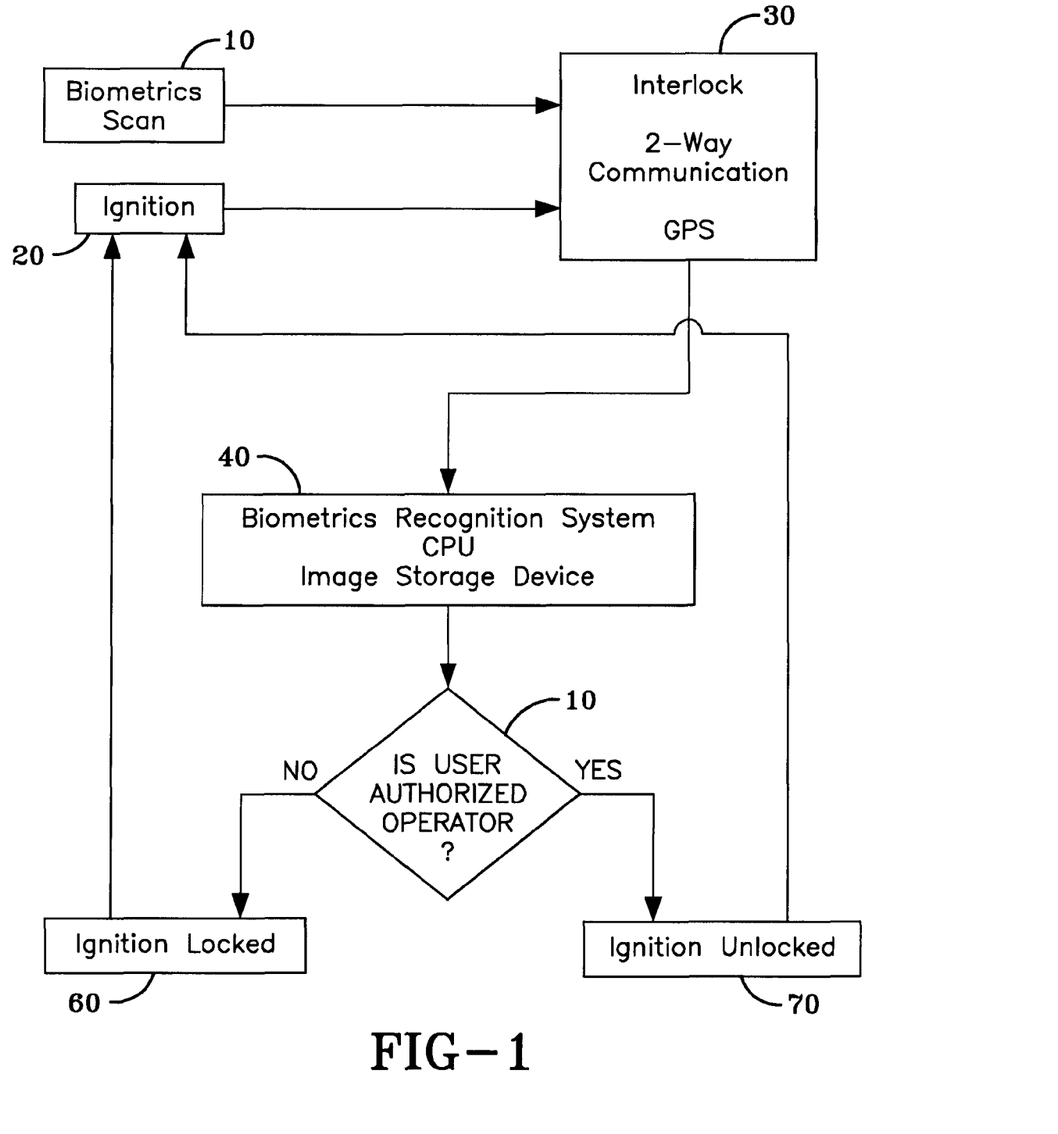
FIG. 1 depicts a flow chart of the present invention when used to determine whether an individual is an authorized operator of a vehicle.

FIG. 1 depicts a flow chart of the present invention when used to determine whether an individual is an authorized operator of a vehicle. In block 10, the individual who is in the operator's seat of the vehicle, usually a motor vehicle such as a truck or automobile, but not necessarily so limited, pushes a button (or inserts a key in the ignition) to activate the system, block 20. A biometrics scan, which is a scan of a feature which is unique to each individual, of the individual is initiated and sent to the interlock system, 30, which system may include an optional GPS system and/or two way communications such as radio communications. The interlock system processes the scan, block 40, using a CPU and an image storage device. The biometrics scan is compared to biometrics images stored in the storage device, block 50. If the biometrics scan is matched to a stored biometrics image, the interlock system acts in conjunction with the ignition to allow the vehicle to operate. If the biometrics scan is not matched, the interlock system acts in conjunction with the ignition system to prevent any initial operation of the vehicle.

Figure 2:
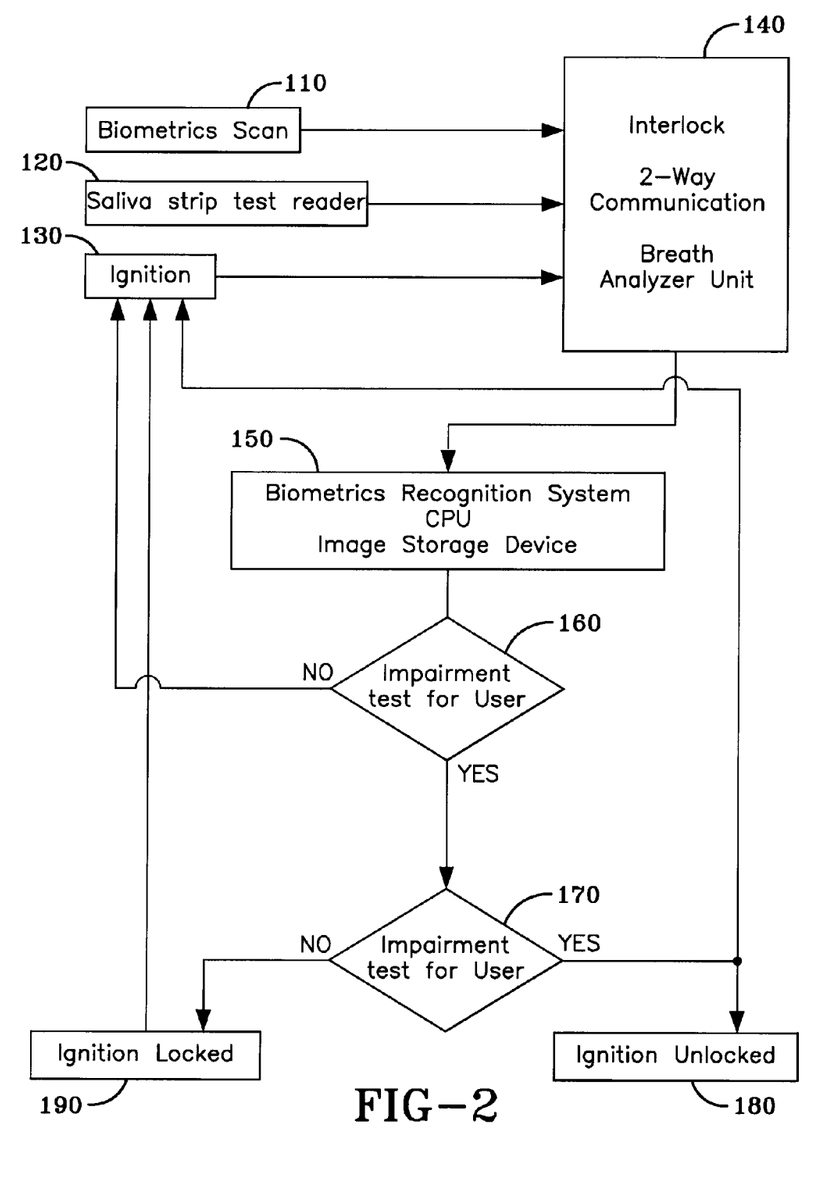
FIG. 2 depicts a flow chart of the present invention when used to determine whether an individual under mandated testing is impaired.

FIG. 2 depicts a flow chart of the present invention when used to determine whether an individual under mandated testing is impaired. Although similar to FIG. 1, it includes additional steps. The system of FIG. 2 includes a biometrics scan 110 that is activated when an individual is seated in the operator's seat. It can be activated by placing a key in the ignition 130, by pushing a button or by a switch installed in the seat. As indicated, interlock 140 includes a breath analyzer unit and a 2-way communications system. A biometrics scan, which is a scan of a feature which is unique to each individual, of the individual is initiated and sent to the interlock system, 140, which system may include an optional GPS system and/or two way communications such as radio communications. The system may also include a saliva strip test reader. The interlock system processes the scan, block 150, using a CPU and an image storage device. The biometrics scan is compared to biometrics images stored in the storage device, block 150. If the biometrics scan is matched to a stored biometrics image, the system then determines whether the individual in the operator's seat must take an impairment test, 160. If the person is not so recognized, the interlock system acts in conjunction with the ignition to allow the vehicle to operate. If the person is so recognizes, the interlock system acts in conjunction with the ignition system to prevent any initial operation of the vehicle until a test is taken. The impairment test may include a saliva strip test reader for use by the individual or the breath analyzer unit, or both. Any other test, such as an ocular scan may also be used. If it is determined that the user is not impaired, 170, then the ignition is unlocked 180. However, if it is determined that the user is impaired, then the ignition is locked and the vehicle is prevented from any operation.

Figure 3:
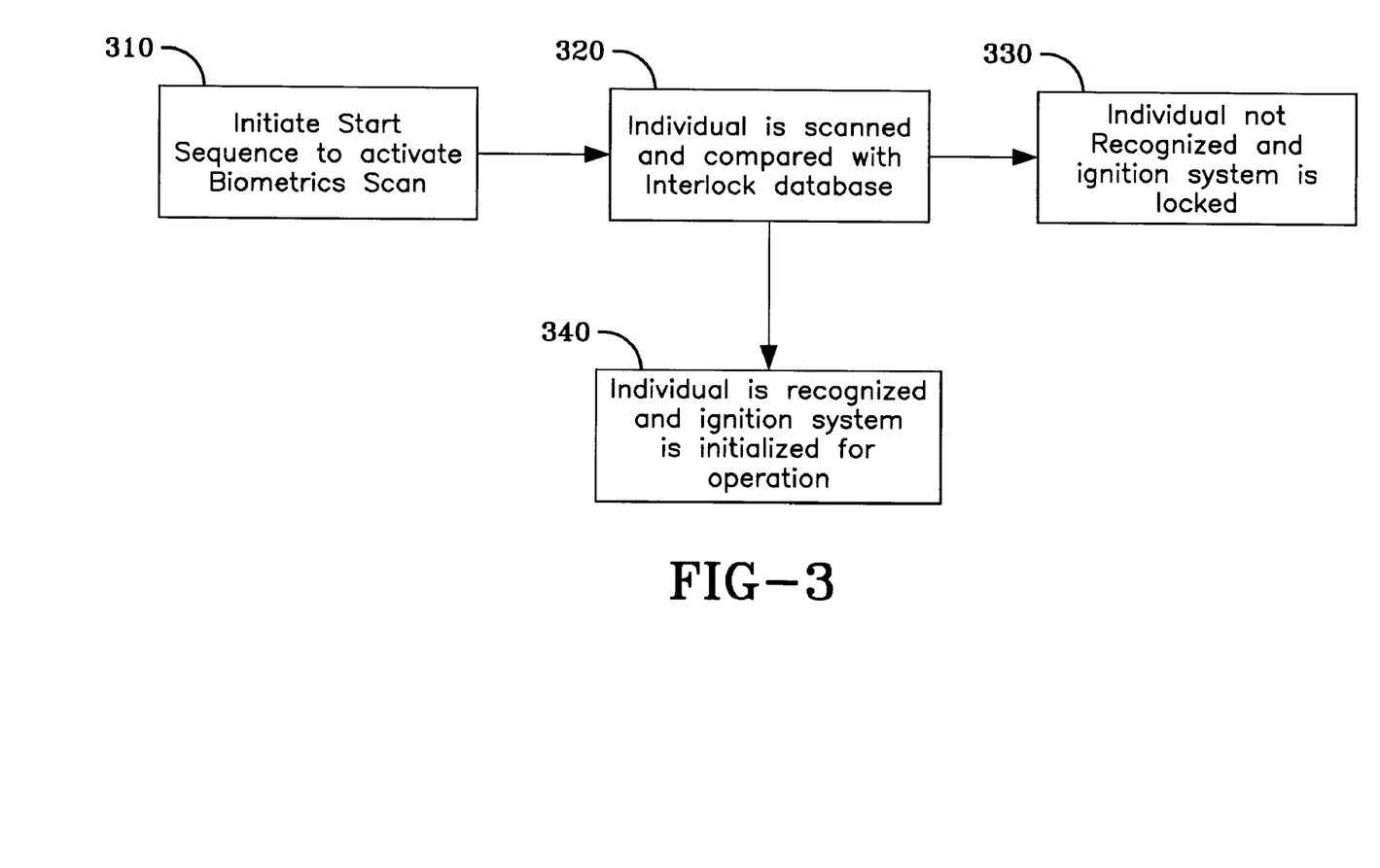
FIG. 3 sets forth the process described in FIG. 1 used to determine whether an individual is an authorized operator of a vehicle.

FIG. 3 sets forth the process described in FIG. 1 used to determine whether an individual is an authorized operator of a vehicle. A person occupying the operator's position initiates the start sequence to activate a biometrics scan, 310. The individual is scanned and the biometrics scan is compared to a corresponding stored biometrics image in the Interlock database 320. If the individual is not recognized, that is, if the biometrics scan does not match a corresponding biometrics image, the interlock system locks the ignition system 330, thereby preventing an unrecognized individual, such as a thief, from operating the system. Of course, as noted elsewhere, the owner of the vehicle can inactivate the interlock system by utilizing a personal identification number (PIN) into the system so that the vehicle can be operated by a third party, such as a valet, for a short period of time. The interlock system can even allow the owner to preselect the short period of time. As indicated in block 340, if the individual is recognized, that is, if the biometrics scan matches the biometrics image stored in the computer, then the ignition system is activated.

Figure 4:
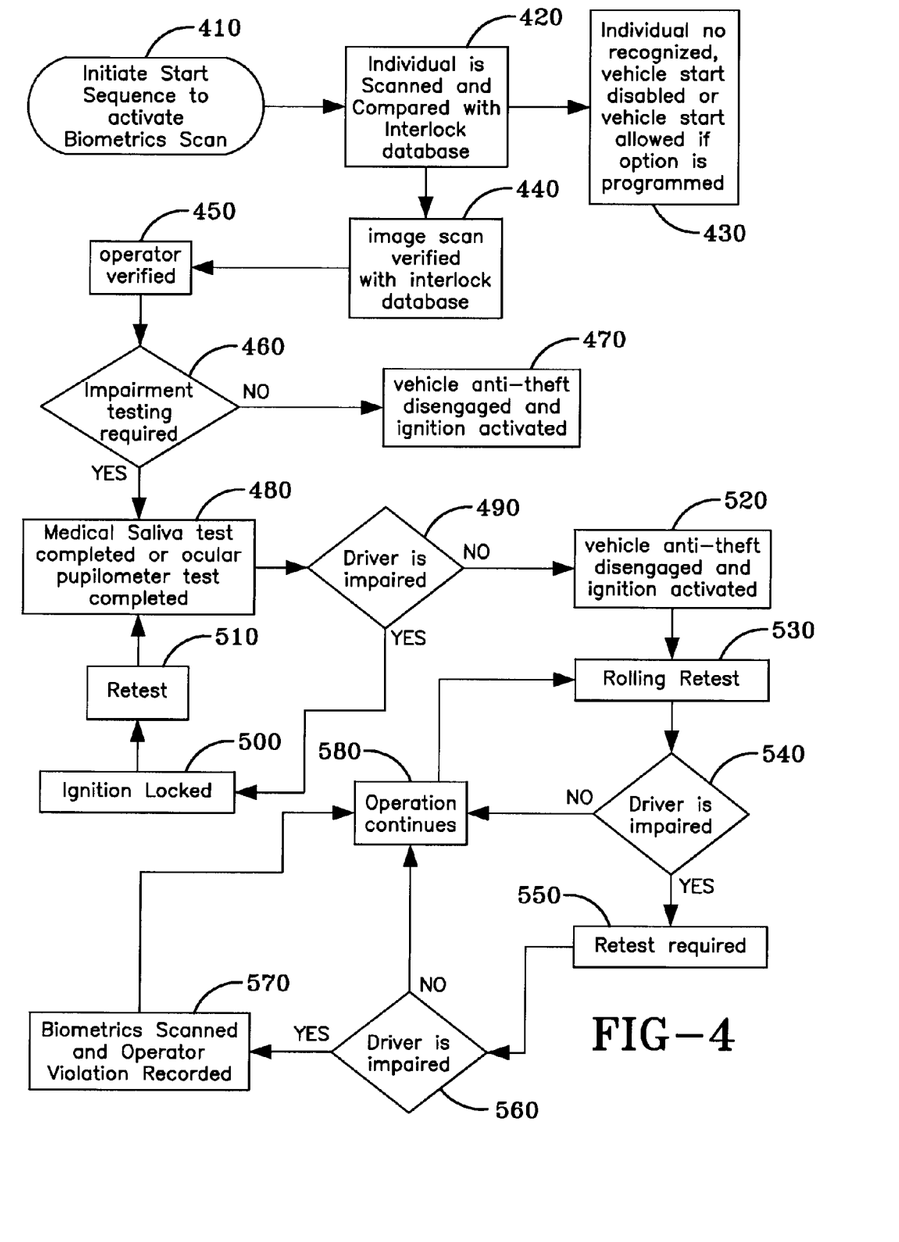
FIG. 4 sets forth the process of FIG. 2 which outlines in additional detail the verification testing of an individual under mandated testing.

FIG. 4 sets forth the process of FIG. 2 which outlines in additional detail the verification testing of an individual under mandated testing. * A person occupying the operator's position initiates the start sequence to activate a biometrics scan, 410. The individual is scanned and the biometrics scan is compared to a corresponding stored biometrics image in the Interlock database 420. If the individual is not recognized, that is, if the biometrics scan does not match a corresponding biometrics image, the interlock system may lock the ignition system 430, thereby preventing an unrecognized individual, such as a thief, from operating the system, or the interlock system may include an option to allow it to be programmed to allow the vehicle to start even if the operator is not recognized. As indicated in block 440, if the individual is recognized, that is, if the biometrics scan matches the biometrics image stored in the computer, then the ignition system is activated. Once the operator is verified, 450, the interlock system the determines whether court-mandated impairment testing of the operator is required 460. If the operator is determined from the data base and memory not to be subject to court-mandated impairment testing, the vehicle interlock system and, if so programmed, anti-theft features are inactivated and the ignition is engaged 470. If, however, impairment testing is required, then the appropriate impairment test is administered 480. This impairment test may require the user to use a breath alcohol detector, or it may be an ocular test, such as a pupilometer test, or it may require the operator to administer a medical saliva test. If testing indicates that the driver is not impaired 490, then the interlock system is inactivated and the ignition is engaged. On the other hand, if testing determined that the driver is impaired 490, the ignition is locked 500, although a retest may be implemented, either automatically or at the operator's request 510. Retest repeats impairment test 480. Once the ignition is activated, 520, the interlock system permits rolling retests 530 of the impairment tests administered in block 480. This rolling retest may be mandated by a court. If the rolling retest indicates that the driver is not impaired 540, normal operation continues 580 and rolling retest 530 is repeated at intervals as determined by a program that controls the interlock. If, however, it is determined that the driver is impaired 540, an immediate retest 550 is required and administered. If the retest indicates that the operator is not impaired 560, operation of the vehicle continues as previously described 580. If however, rolling retest indicates that the driver is impaired 560, the biometrics scanner is activated and an image of the operator is recorded 570 in the memory of the interlock system so that the violation can be reported. Even though the interlock system could shut down the vehicle, this may create an even more dangerous situation so operation of the vehicle is permitted to continue 580.

The system can also incorporate General Packet Radio Service (GPRS) and Global System for Mobile Communication (GSM) to provide additional capabilities. GPRS is integrated into GSM Release97 and newer releases. CDMA-Code Division Multiple Access—2G networks and W-CDMA—Wideband Code Division Multiple Access—(higher speed protocol using 3G networks) can also be utilized.

This technology is widely used for two way communication and WAP (Wireless Application Protocol), Short Message Service (SMS), and MMS (Multimedia, Messaging Service), and for Internet, such as e-mail service and World Wide Web access.

This communication feature integrated as an add-on component to the expandable ignition interlock base design platform can be used to troubleshoot and remotely service the ignition interlock while in field operation. The design is currently working on either a 2G network or 3G network which provides faster data transmission time.

When equipped with these communications capabilities, it is possible for the interlock system of the present invention to communicate with a remote service and monitoring location while the interlock system is in active duty status in an operator's car. For equipment service reasons, using GSM/GPRS/CDMA/WCDMA-type technology, a company service monitoring center can contact an operator's unit to download a summary data log report or an entire data log report for the objective of resolving possible issues. While the log data report can be customized, one embodiment includes a data log report listing diagnostic line items of key equipment functions or possible unit malfunctions.

One potential service issue can be a malfunction in any major component of the ignition interlock, which would cause an operator to have difficulty with the normal operation of their interlocked vehicle. To avoid an authorized operator from being stranded due to an inoperable vehicle situation resulting from a malfunctioning interlock installed in the vehicle, a service-monitoring technician using two-way communication can remotely correct a problem or advise an operator to take a proper course of action.

Another potential service issue is an interlock in a 'recall to service center' situation where an operator has exceeded a jurisdictional required preset interlock program violation limit. Once an operator of an ignition interlock unit exceeds it's permissible violation limits, the ignition interlock will enter into a grace period count down mode before the ignition interlock disables the vehicle from starting. This feature requires the operator to physically report to a service center with their vehicle for a data log download and a software violation limit reset. With two-way communication, the ignition interlock can also be programmed to dial out to a service monitoring center to provide notification of the exceeded violation limit status. Alternatively, an operator can make a phone call requesting service when such an event occurs. Two-way communication between the interlock system and the service-monitoring center can allow a factory technician to remotely download the data log report for data retrieval and then perform a remote violation reset function saving both the technician and the operator lost time and difficulties. The emphasis on two-way communication with the ignition interlock equipment is based upon the ability to provide timely and cost efficient service for the operator of the vehicle or apparatus.

Incorporation of GPS—Global Satellite Communication

With broad commercially available and affordable GPS locator technology offered by carriers such as mobile cell phone service companies, communication and location information is readily integrated into and monitored by the interlock system. GPS technology can perform around the clock, and location coordinates can also be recorded in conjunction with a specific event by software triggers. All coordinates can be recorded with longitude and latitude degrees.

An added feature of the expandable base platform design for the ignition interlock of the present invention can conveniently permit it to function with an incorporated on-board GPS device, such as a GPS chip or a GPS chip operating in conjunction with memory, which can record all location information at a predetermined frequency, such as at all data log events, or at a desired time interval. The location readings, in longitude and latitude if desired, can be included in the downloadable ignition interlock data log report. With the use of a GSM/CDMA reporter, an operator's location can be identified and the operator notified to report to a predetermined location, such as a service-monitoring center, for assistance in technical or interlock program difficulties. In case of an emergency, an operator can utilize the ignition interlock to send report data out to a service monitoring location verifying their location.

Thus, the facial biometric ignition interlock device of the present invention 3-D or 4-D recognition enables substantially instantaneous positive identification of an operator of a vehicle or an apparatus. "Substantially instantaneous" as used herein means instantaneously or with a few seconds, but less than about 2 minutes, preferably in about 2 seconds for infrared facial biometrics. Current state-of-the-art hardware used in the system of the present invention requires additional time for selected ocular tests, which can uniquely identify an individual by at least one feature of the eye selected from the group consisting of an iris, a retina, a cornea, and a blood vessel pattern. The 3-D or 4-D facial biometric selected is unique to an individual. Preferred biometrics include an infrared facial scan or an eye scan, the eye scan most preferably including some variant of pupilometry. For example, scanning of at least one of the iris, the retina, the cornea or the blood vessel pattern may be used for biometric identification of an individual, and an EyeCheck™ scan may be used for impairment screening.

While the facial biometric ignition interlock system of the present invention using 3-D or 4-D recognition has been developed for use in vehicles operated by individuals under court-ordered supervision for driving while impaired, while the present invention provides a sophisticated system that can expand the ability of law enforcement to monitor individuals under court-ordered supervision for alcohol abuse. The facial biometric identification system of the present invention in conjunction with the interlock can also be used as an anti-theft device for vehicles. Three or four-dimensional biometric images such as the infrared facial scan or the iris scan of the eye of authorized operators can be stored in memory. Attempts to activate the vehicle will result in activation of the camera or other appropriate scanning equipment which will scan the individual in the operator's seat. The infrared scanned image will then be compared to the images stored in memory. Since the 3-D and 4-D scans can positively identify an individual if the scanned image does not match an image stored in memory, the interlock system will be activated preventing operation of the vehicle. Scanning may be repeated at periodic intervals while the vehicle is being operated to confirm that the operator has not been changed and continues to be an authorized operator. Due to safety concerns, if during a retest, it is ascertained that the operator whose image was most recently scanned is not an authorized operator, a warning can be generated to inform the operator that the vehicle will be automatically disabled within a predetermined time to permit the operator of the vehicle to safely position it outside of the main traffic flow.

In addition, or alternatively if provided with communications capability, the unit can contact the owner that the vehicle is being operated by an unauthorized user. If the vehicle has been stolen, the owner can report the theft to the police. If the interlock system is additionally equipped with a GPS, the location of the vehicle can also be reported. Of course, authorized operators will be able to enter a temporary code to override the system for preselected periods of time to permit operation of the vehicle by mechanics, valets and the like. The system can be expanded to include a breath alcohol analyzer component at a later time, if it is determined by a court-order that the breath alcohol monitoring is required.

The present invention can also be expanded beyond the court-ordered breath alcohol monitoring and can be used for other impairments. Specifically, pupilometry can be used to monitor the pupils for dilation and/or pupil movement. The latter uses an infrared device to monitor an aspect of the eye. However, unusual pupil dilation and/or unusual pupil movement can be a sign of physical impairment resulting from drugs or perhaps fatigue. Any indication of impairment can be sufficient for activation of the interlock system to prevent vehicle or apparatus operation.

The interlock system of the present invention is responsive to 3-D or 4-D image matching that provides a positive identification, and then required, to test for indicia of impairment. Usually, the impairment testing is court-ordered breath alcohol tests, but as noted above, may include a determination of other measurable features, such as pupil dilation or pupil movement. The interlock system may include separate components hard-wired to the ignition system. However, with increasing sophistication of automotive vehicles, most vehicles include a sophisticated computer that controls many aspects of vehicle operation. The interlock system may be a microchip or a software subroutine that is in communication with the vehicle computer and provides a signal that permits vehicle ignition or one that immobilizes vehicle operation when predetermined conditions are not met.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A breath alcohol ignition interlock device, comprising:
 a 3-D infrared scanning device for performing a biometrics infrared facial scan of an individual positioned proximate to the device and proximate to an ignition of a mechanical device, wherein the 3-D scanning device analyzes both hard and soft tissue to generate a real-time identity scan of the individual using infrared radiation;
 a CPU having memory capabilities;
 3-D biometrics infrared hard and soft tissue scan images obtained using infrared radiation of at least one authorized operator of the mechanical device stored in the memory;
 means for comparing the stored infrared hard and soft tissue scan images of an authorized operator of the mechanical device from memory with the real-time scan of the individual obtained using infrared radiation to determine that the individual is one of the authorized operators;
 a detection device in communication with the CPU to ascertain the presence and amount of a controlled substance consumed by the individual; and an interlock device in communication with the detection device and the CPU, wherein the interlock device prevents operation of the mechanical device when the means for comparing stored hard and soft tissue images with the real-time scan indicates that the individual is not one of the authorized operators and when the detection device indicates the presence and amount of a controlled substance consumed by the individual exceeds a legal limit for the controlled substance.

2. A breath alcohol ignition interlock device, comprising:
 a 4-D infrared scanning device for performing a real-time biometrics infrared facial scan of an individual positioned proximate to the device and proximate to an ignition of a mechanical device, wherein the 4-D scanning device analyzes both hard and soft facial tissue of the individual, using infrared radiation to generate a real-time scan of the individual;
 a CPU having memory capabilities;
 4-D biometrics infrared facial scan images of at least one authorized operator of the mechanical device stored in the CPU memory;
 means for comparing the infrared facial scan images of the at least one authorized operator of the mechanical device stored in the CPU memory with the real-time infrared facial scan of the individual positioned proximate the ignition of the mechanical device to determine whether the individual is one of the authorized operators;
 a detection device in communication with the CPU to ascertain the presence and amount of a controlled substance consumed by the individual; and
 an interlock device in communication with the detection device and the CPU, wherein the interlock device prevents operation of the mechanical device when the means for comparing stored facial images of the at least one operator with the real-time facial scan of the individual indicates that the individual is not one of the authorized operators or when the detection device indicates the presence and amount of a controlled substance consumed by the individual exceeds a legal limit for the controlled substance.

3. An interlock system, comprising:
a scanning device for performing a biometrics scan of a facial feature of an individual positioned proximate to the scanning device and proximate to an ignition of a mechanical device, wherein the scanning device analyzes a biometric facial characteristic that is unique to the individual, the characteristic selected from the group consisting of an infrared facial scan of hard and soft tissue, and a real-time infrared ocular biometrics scan of an ocular feature, to provide a real-time biometrics scan;
a CPU;
a memory storage device;
a biometrics image of the hard and soft tissue of at least one operator authorized to operate the mechanical device, the image stored in the memory storage device;
means for comparing the biometrics image of at least one operator stored in the memory storage device with a real-time biometrics scan of the individual proximate the ignition generated by the scanning device to ascertain that the individual is an authorized operator;
an interlock unit in communication with the CPU and the means for comparing the stored biometrics image with the real-time biometrics scan.

4. The interlock system of claim 3 wherein the interlock unit prevents operation of the mechanical device when the means for comparing the stored biometrics image of the authorized operator with the real-time biometrics scan of the individual indicates that the individual proximate the ignition is not one of the authorized operators of the mechanical device.

5. The interlock system of claim 3 wherein the CPU and the memory storage device are combined in a single integral unit.

6. The interlock system of claim 3 further including a memory storage device in electronic communications with the CPU.

7. The interlock system of claim 3 wherein the real-time biometrics scan and the stored biometrics image include a 3-D infrared scan of the biometric characteristic of the individual proximate the ignition and the stored 3-D image of the of the biometric characteristic of at least one authorized operator.

8. The interlock system of claim 3 wherein the real-time biometrics scan and the stored biometrics images include a 4-D biometric scan of the facial feature of the individual proximate the ignition and the 4-D biometric image of the facial feature of at least one authorized operator.

9. The interlock system of claim 3 wherein the stored, biometrics image further includes an infrared ocular image of measured pupil dilation and measured pupil movement, and, the real-time infrared biometrics facial scan includes the infrared ocular biometrics scan of pupil dilation and pupil movement of the individual proximate the ignition that compares the stored measured pupil dilation and the stored measured pupil movement of at least one operator with the real-time pupil dilation and the real-time pupil movement of the individual, wherein the comparison determines one of impairment and non-impairment.

10. The interlock system of claim 3 wherein the real-time infrared ocular biometrics scan of the individual and the stored biometrics image of the facial feature of at least one operator include a biometrics scan of at least one feature of the eye selected from the group consisting of an iris, a retina, a cornea, and a blood vessel pattern.

11. The interlock system of claim 10 wherein the interlock unit prevents operation of the mechanical device when the scanning device performing the biometrics scan of the facial feature indicates that the individual proximate the ignition is not at least one authorized operator of the mechanical device.

12. The interlock system of claim 3 wherein the system further includes a detection device in communication with the CPU to determine the presence of a controlled substance consumed by the individual positioned proximate the device and the ignition of the mechanical device and to identify the individual using a real time infrared biometrics scan.

13. The interlock system of claim 12 wherein the detection device in communication with the CPU further determines whether the individual positioned proximate the device and the ignition is impaired.

14. The interlock system of claim 13 wherein the means for comparing further determines that the individual proximate the ignition is an authorized user that is required to utilize the detection device to ascertain whether the individual is impaired, and the interlock device prevents operation of the mechanical device when the individual is an authorized user required to utilize the detection device, until the individual utilizes the detection device.

15. The interlock system of claim 14 wherein the interlock device prevents operation of the mechanical device when the individual positioned proximate the interlock device utilizes the detection device and the detection device determines the individual is impaired.

16. The interlock system of claim 13 wherein the scanning device performs the real-time ocular biometrics scan of the ocular feature of the individual proximate the ignition, and the memory storage device includes the image of the ocular feature of at least one operator authorized to operate the mechanical device, and wherein the detection device includes a saliva test strip reader used in conjunction with a saliva test strip to test saliva provided by the operator to determine impairment.

17. The interlock system of claim 13 wherein the detection device utilizes the real-time infrared ocular biometrics scan wherein the real-time ocular biometrics scan measures pupil eye dilation and pupil eye movement by comparison against a baseline measurement of the ocular biometrics image stored in memory to determine whether the individual positioned proximate the device and proximate to the ignition is impaired.

18. The interlock system of claim 17 wherein the real-time infrared biometrics scan of the pupil eye dilation and the pupil eye movement are compared against a baseline measurement of the pupil eye dilation and the pupil eye movement stored in the memory storage device to determine whether the individual positioned proximate the device and proximate to the ignition is impaired, and wherein real-time biometrics scanning is performed as a retest during vehicle operation.

19. The vehicle interlock device of claim 13 further including a two- way communications system wherein the two-way communications system transmits recorded positions stored in memory and receives notification for an operator to report to a predetermined location.

20. The interlock system of claim 12 wherein the detection device analyzes a breath sample of the individual positioned proximate the ignition to determine a blood alcohol level.

21. The interlock system of claim 12 wherein the detection device performs a retest of the individual proximate the ignition for impairment during operation of the mechanical device, and wherein a real-time image of the individual is stored in the memory storage device when impairment is determined.

22. The interlock system of claim 3 further including a GPRS device that determines the location of the vehicle, records the location of the vehicle at a predetermined frequency, stores the recorded location in a memory storage device, and transmits the real-time location of the vehicle.

* * * * *